US00PP10548P

United States Patent [19]

Bjorge et al.

[11] Patent Number: Plant 10,548

[45] Date of Patent: Aug. 11, 1998

[54] 'FA 11' PEACH TREE

[75] Inventors: Annette Bjorge; Randy Bjorge, both of Coloma, Mich.

[73] Assignee: International Plant Management, Lawrence, Mich.

[21] Appl. No.: 738,254

[22] Filed: Oct. 28, 1996

[51] Int. Cl.[6] ..... A01H 5/00

[52] U.S. Cl. ..... Plt./43.2

[58] Field of Search ..... Plt./43.2

*Primary Examiner*—James R. Feyrer

[57] ABSTRACT

A new peach variety, *Prunus persica*, (hereinafter referred to as the 'FA 11' peach tree variety) which was developed by Annette and Randy Bjorge in a breeding program at Fruit Acres Farm in Coloma, Mich., having the following combination of unique and desirable features:

1. A fruit with excellent shipping and storage qualities.
2. A fruit maturing 5 days after the 'Redhaven' peach.
3. A substantially round fruit with clear yellow flesh and an attractive bright red mottled stripe covering 95% of the fruit at maturity.
4. A fruit with flesh that does not brown when cut.
5. A fruit and tree with excellent resistance to bacterial spot.
6. A tree and blossom with hardiness superior to 'Redhaven'.

3 Drawing Sheets

ORIGIN OF THE VARIETY

The new variety of peach tree 'FA 11' was developed by Annette and Randy Bjorge in a peach breeding program at Fruit Acres Farms, 2559 Friday Road, Coloma, Mich. 49038. The 'FA 11' peach tree was developed as a first generation cross between 'Fayette' and 'Newhaven', two established, non-patented, commercial varieties. The parent tree was grown and maintained in a peach tree breeding orchard in Fruit Acres Farms.

This new and distinct variety of peach tree has been asexually propagated by budding at Fruit Acres Farms in Coloma, Mich. The asexual propagation demonstrates that such reproduction of the characteristics of the tree are consistent and are established and transmitted through succeeding generations.

SUMMARY OF THE VARIETY

The new and distinct variety of peach tree is of upright, vigorous, very hardy growth with medium density and is a regular and very productive bearer of peaches. The fruit of the new variety is characterized by round, substantially 95% rich red fruits with a mottled striped color pattern that present a very attractive appearance. The fruits have firm flesh and are resilient to the extent that they may be handled and packaged mechanically without damaging the same for shipment. This results in less spoilage and a greater market value. The flesh of the fruits of the new variety does not brown when cut. The fruits of the new variety have a recessed pistil point which avoids damage during picking and handling. The new variety is a very heavy, consistent producer and requires several pickings. The tree and fruits of the new variety exhibit good resistance to Bacterial Spot and are very cold hardy. The fruit matures in the middle of the peach growing season in Southwestern Michigan. It ripens 5 days after the established commercial variety, 'Redhaven'.

BRIEF DESCRIPTION OF THE PHOTOGRAPHS

The accompanying photographs show typical specimens of the new variety in color as nearly true as it is reasonably possible to make the same in color illustrations of this character. The specimens were photographed in Van Buren and Berrien counties of Southwestern Michigan.

FIG. 1. illustrates specimens of the fully ripened fruit and foliage of the new variety.

FIG. 2. illustrates blooms of the new variety.

FIG. 3. Illustrates two specimens of the new variety. The upper specimen is bisected along the suture, the lower specimen is bisected as a ninety-degree angle to the plane of the suture. The color and forms of the flesh, pit and pit cavity are illustrated.

DETAILED DESCRIPTION OF THE VARIETY

Figure 1:
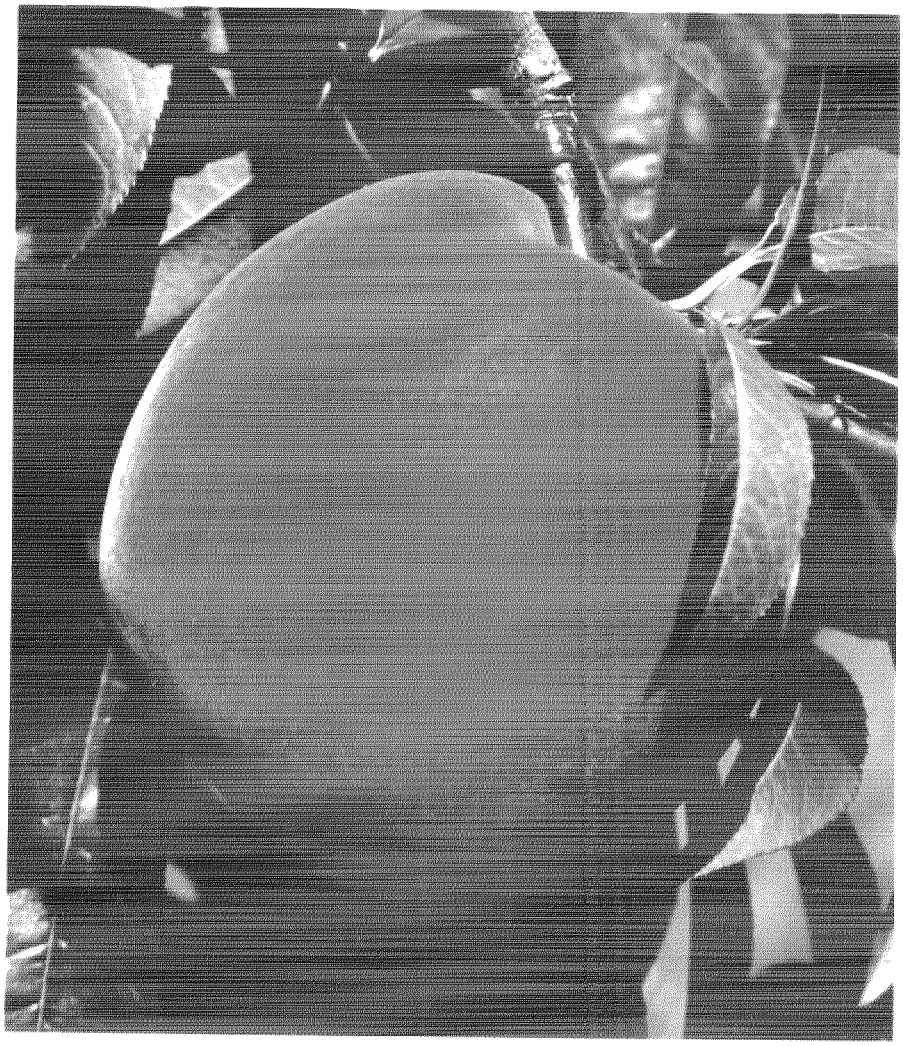
Figure 2:
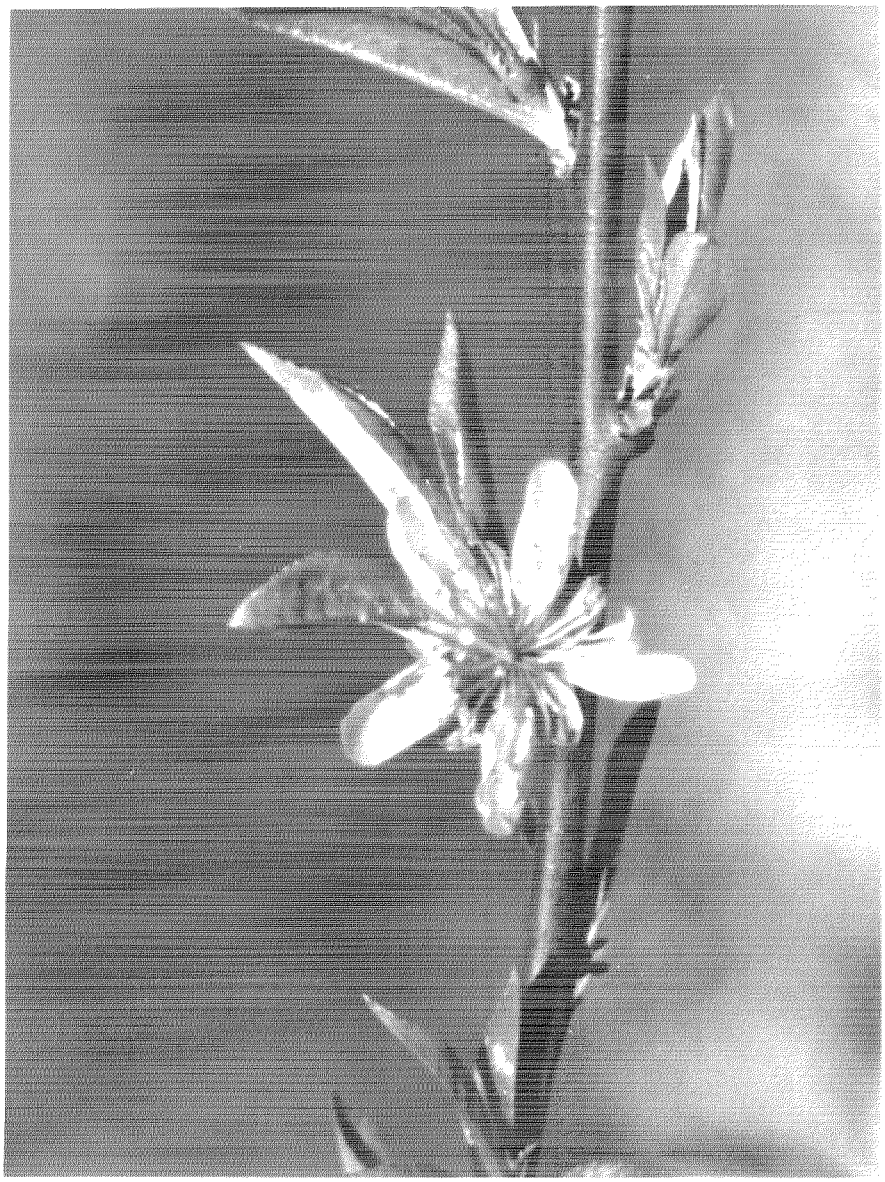
Figure 3:
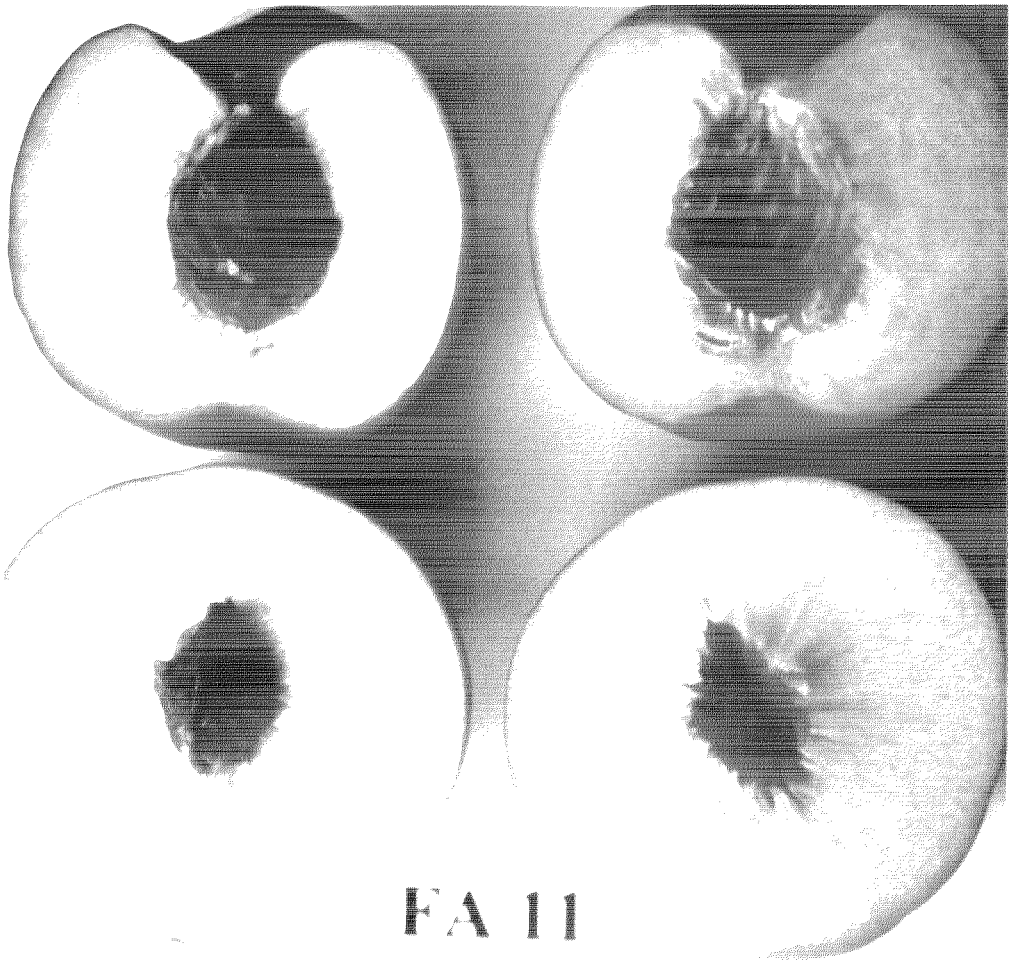

The following description of the fruit and foliage of the new variety is based on observations of specimens grown in Berrien and Van Buren County of southwestern Michigan. The color terminology is in accordance with The Royal Horticultural Society Colour Chart, published by The Royal Horticultural Society of London, England.

Tree:

*Age of the specimen.*—15 years

*Height.*—Unpruned 4.3M.

*Width.*—Unpruned 5M.

*Size.*—Large.

*Vigor.*—Medium, heavy foliage. Requires spring pruning and heavy thinning to counteract its tendency to overproduce.

*Density.*—Medium, internode length averages 2 cm.

*Form.*—Moderately spreading. Major scaffold branches form 45° to 50° angles to the trunk. Will form a central leader if left unpruned. Does not require supplemental support.

*Production.*—Very heavy producer, requires 2 to 3 pickings with 70% of the crop being mature for the first picking and the remainder becoming mature for the last pickings. Is much more productive than its parents or 'Redhaven'.

*Bearing.*—Annual. Harvest season lasts 5 to 7 days. Fruits will hold on the tree for 10 days at maturity.

*Disease resistance.*—Good resistance to Bacterial Spot and Peach Canker.

*Cold hardiness.*—very hardy.

Trunk:

*Size.*—Large.

*Surface.*—Medium smooth.

*Lenticils.*—Large.

*Color.*—Gray 201 A.

Leaves:

*Size.*—Length 37mm, width 155mm, not including petiole.

*Form.*—Wavy, apex sharply acute, base acute.

*Thickness.*—Medium.

*Texture.*—Medium.

*Margin.*—Crenate.

*Petiole.*—Length 8–10mm, 0.7mm wide.

*Glands.*—Reniform, 2–5, average 4, located on upper petiole and leaf base.

*Color.*—Upper surface Green 147 A, lower surface Green 147 B.

*Stipules.*—None.

Flower buds:

*Size.*—Medium.

*Length.*—Medium.

Flowers:

*Blooming period.*—April 8 to 15 in Coloma, Mich.

*Presentation.*—Non showy.

*Petals.*—5 in number, curved inward, 13mm long, 10mm wide, Red-Purple 73 A.

*Stamens.*—37 in number, Red-Purple 74 D.

*Pollen.*—Present, self fertilizing.

*Pistil.*—17mm in length, White 155 A.

Fruit:

*Maturity when described.*—Firm ripe.

*Date of first picking.*—August 14 in southwestern Michigan, 5 days after 'Redhaven'.

*Date of last picking.*—August 21 in southwestern Michigan.

*Size.*—65 to 80mm.

*Form.*—Round, slightly unequal halves to slightly oblong.

*Suture.*—Clean, very slight raised indentation on some.

*Pistil point.*—Recessed.

Skin:

*Thickness.*—Medium.

*Texture.*—Fine.

*Tendency to crack.*—None.

*Down.*—Little.

*Color.*—80% Red 45 A with a mottled stripe of Red 53 B over a background of Yellow-Orange 22 B.

Flesh:

*Texture.*—Semi-firm.

*Aroma.*—Medium, not pungent.

*Fibres.*—Few, small, tender, not conspicuous or noticeable in eating.

*Color.*—100% Yellow-Orange 20 B.

*Coloration at pit.*—Very slight amount of pinkish-red around pit.

*Eating quality.*—Medium, sweet with mild acid.

Stone:

*Size.*—Length 33mm, width 25mm, thickness 17mm.

*Form.*—Ovate.

*Apex.*—Pointed.

*Sides.*—Equal.

*Base.*—Flat.

*Surface.*—Pitted to furrowed throughout.

*Color.*—Grayed-orange 172 A.

*Type.*—Freestone.

*Tendency to crack.*—None.

Use: Desert, commercial and fresh market.

Shipping quality: Excellent.

Keeping quality: Excellent, will hold for 4 weeks in common cold storage.

Disease resistance: Good resistance to Bacterial Spot and Peach Canker.

I claim:

1. A new and distinct variety of peach tree, *Prunus persica,* substantially as herein shown and described, characterized particularly as to novelty by the unique combination of vigorous, upright, open, very hardy, medium density, regular bearing tree, with resistance to bacterial spot and peach canker, producing freestone fruits having clear yellow, non-browning flesh and substantially round, firm, 95% striped, bright red skin color at maturity which occurs 5 days after 'Redhaven' peach.

* * * * *